United States Patent [19]

Lyons et al.

[11] Patent Number: 4,803,187

[45] Date of Patent: Feb. 7, 1989

[54] ALKANE OXIDATION CATALYSTS

[75] Inventors: James E. Lyons, Wallingford; Paul E. Ellis, Jr., Downingtown; Harry K. Myers, Jr., Cochranville; George Suld, Springfield; Wayne A. Langdale, Milmont Park, all of Pa.

[73] Assignee: Sun Refining and Marketing Company, Philadelphia, Pa.

[21] Appl. No.: 76,570

[22] Filed: Jul. 20, 1987

[51] Int. Cl.$^4$ .......................... B01J 27/24; B01J 27/14
[52] U.S. Cl. .................................. 502/200; 502/208; 568/399; 568/910
[58] Field of Search ............................... 502/200, 208

[56] References Cited

U.S. PATENT DOCUMENTS

| | | | |
|---|---|---|---|
| 3,998,876 | 12/1976 | Kato et al. | 502/200 |
| 4,001,316 | 1/1977 | Ishimi | 502/200 |
| 4,026,950 | 5/1977 | La Ludec | 502/200 |
| 4,043,934 | 8/1977 | Shuler et al. | 502/200 |
| 4,182,745 | 1/1980 | Nishida et al. | 502/208 |
| 4,419,270 | 12/1983 | Veshima et al. | 502/208 |
| 4,454,244 | 6/1984 | Wolfermann | 502/208 |
| 4,528,398 | 7/1985 | Callahan et al. | 502/200 |

Primary Examiner—William R. Dixon, Jr.
Assistant Examiner—David M. Brunsmen
Attorney, Agent, or Firm—J. Edward Hess; Donald R. Johnson

[57] ABSTRACT

Heteropolyacids or polyoxoanions promoted with azide, such as $K_6PW_{11}VO_{40}N_3$, useful in the liquid phase oxidation of alkanes.

5 Claims, No Drawings

ALKANE OXIDATION CATALYSTS

This invention relates to the oxidation of alkanes in the liquid phase with polyoxoanions (POAs) or heteropolyacids (HPAs) which have been promoted or otherwise modified to improve their effectiveness, and to certain of such catalysts.

BACKGROUND OF THE INVENTION

The use of POAs and HPAs for the catalytic air oxidation of alkanes such as butane is known. [See, for example, M. Ai, Partial Oxidation of n-Butane with Heteropoly Compound-based Catalysts, Proceedings of the 8th International Congress on Catalysts, Berlin, 1984, *Verlag Chemie* Vol. 5, page 475]. However, these oxidations have been high temperature, vapor phase reactions which are, by their nature, prone to by-products, including carbon oxides (CO and $CO_2$) and water, or have been oxidations of alkenes and alcohols which are quite easy to oxidize. In addition, selective, low temperature, liquid phase oxidation of alkanes to alcohols are notoriously more difficult to effect than vapor phase oxidation, whatever the catalyst.

HPAs and POAs, both in general and those used in our invention, and their preparation are thoroughly described in *Heteropoly and Isopoly Oxo-metalates*, Pope et al, Springer-Verlag, New York 1983. In order to clarify the terminology used in the art, consider first a specific precursor used in our invention, $H_3PW_{12}O_{40}$. Since the cations in this material are hydrogen, the compound is a heteropolyacid. If the cations are not hydrogen but are metals such as an alkali metal, potassium, sodium, or lithium, or are ammonium, as in $K_3PW_{12}O_{40}$ or $(NH_4)_3PW_{12}O_{40}$, then it is obviously no longer an acid, and is referred to as a polyoxoanion.

As described in Pope, HPAs and POAs are cage-like structures with a primary, generally centrally located metal atom(s) surrounded by the cage framework which contains a plurality of other atoms, the same or different, bonded to oxygen atoms. Since the central metal atom is different from the other atoms, it is described as "hetero." The other metal atoms are transition metals and have oxygen bonding such as

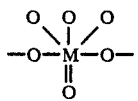

SUMMARY OF INVENTION

Our invention involves HPA and POA catalyzed, selective oxidation of alkanes with oxygen in the liquid phase at relatively mild conditions (usually under 200° C.) to a product rich in alcohol and with little or no burn of alkane to carbon oxides. Our HPAs and POAs are promoted with certain metals and/or with an azide and may possess certain other modifications from a "conventional" HPA or POA.

DETAILED DESCRIPTION

Our invention deals with improvements to HPAs (and POAs thereof) having the general formula $H_e(X_kM_nO_y)^{-e}$ where X, the central atom is preferably phosphorous, but others such as antimony, silicon, and boron are also suitable as are the generally known central atoms of HPAs, i.e., the group IIIA-VIA elements. Subscript k is preferably 1 but can be as high as 4–5. M is one or more transition metals (thus the HPA can be referred to as a transition metal HPA), usually molybdenum or tungsten, and n will vary from 5–20. Subscript y is usually 40 but can be as low as 18 or as high as 62. In a preferred HPA, $k=1$, $n=12$ and $y=40$ as in $H_7PMo_8V_4O_{40}$. These and similar HPAs are shown in the aforesaid Pope reference. Most of our catalysts are of the Keggin structure and its isomers, as described in Pope, but other structures such as the Dawson structure also are suitable.

HPAs are conventionally made by dissolving the metal oxides in the desired proportion in water, adjusting the pH to approximately 1–2 with acid (e.g. HCl) to provide the necessasry $H^+$ cations and then evaporating water until the HPA precipitates. If the POA is desired, a salt such as KCl is added and the POA precipitates, without need for the evaporation step. The desired proportion of the metal oxides added will vary somewhat from the theoretical amount required for the desired product, because in the precipitation step they do not precipitate in those exact same ratios. However, this is a matter of routine testing and adjustment. The existence of the HPA structure, i.e., the metal oxygen bonds, is confirmed by their characteristic NMR and/or IR spectra, which as explained in Pope supra, are now known for the various HPAs.

We have found that molybdenum and tungsten HPAs and POAs have little, if any, activity for low temperature, liquid phase alkane oxidation, but if vanadium or certain other metals are incorporated into the framework in place of an M atom, a marked increase in activity is obtained. Thus, $H_9PW_6V_6O_{40}$ is significantly more active than $H_3PW_{12}O_{40}$ and $K_9PMo_6V_6O_{40}$ is more active than $K_3PMo_{12}O_{40}$. Suitable promoters other than vanadium include, preferably, titanium, niobium and rhenium. The number of metal atoms replaced with the promoter can be as many as 12, preferably 6–8, but can be as low as 3–6 or even 1.

A further aspect of the invention is the introduction of azide into the HPA or POA, which forms a new class of surprisingly active catalysts for selective alkane oxidation, with little burn to carbon oxides. This type of catalyst promotion can be achieved by reacting the HPA or POA with, e.g., sodium azide for several hours at 50°–100° C. or by carrying out the oxidation reaction in the presence of the two components, i.e., the HPA or POA and the azide. The entry of the azide ($N_3^{-1}$) into the cage structure is confirmed by IR analysis in which the frequency of IR absorption corresponds to the N-N stretch in the bound azide. The azide can be introduced into the HPA or POA with or without the aforesaid metal promotion and with or without framework substitution as hereinafter described. Our invention also involves such previously unknown and surprisingly effective azide catalysts. Consistent with the formula given earlier, these azide catalysts can be represented by the formula $H_{(e+x)}(X_kM_nO_y)^{-e}(N_3)_x$ and polyoxanions thereof, wherein X, k, M, n and y are as described above and x is 1–4 preferably 1 or 2.

A further aspect of the invention involves another mechanism which may improve the catalytic activity of the basic HPA or POA for alkane oxidation. This feature is the replacement of an M=O in the framework around the central or principal atom with a transition metal atom. Thus instead of $(O-)_5M=O$ at a specific site in the framework, we might have $(O-)_5M_1$ where M and $M_1$ are different metals. In terms of formula, if an M=O site in $K_3PMo_{12}O_{40}$ is replaced with chromium, we have $K_4PMo_{11}CrO_{39}$.

These framework substituted HPAs or POAs are prepared by a two-step procedure. The first step is the removal of the M=O unit which yields what is known in the art as a lacunary or defect HPA, the second step is the insertion of the new metal. These procedures are known and are generally as follows: A Keggin type HPA, for example, is dissolved in water and the pH is then adjusted (if necessary) to less than 5. The solution is then treated with base at, e.g., 75° C., and at a certain critical pH, one M=O unit is eliminated from the structure. The pH is raised further until, at a second critical pH, two more M=O units are eliminated. Addition of, say, ferrous sulfate will replace the defect M=O sites, i.e., those eliminated, with iron and the framework substituted POA is then precipitated by addition of a salt such as KCl. The resultant crystalline framework-substituted POA is then water washed.

The critical pHs at which M=O units are eliminated have been determined for many HPAs and can be found in the literature, as well as the general kinetic method for determining these pHs.

The metals available for framework substitution are the transition metals previously described, preferably Groups IVB-VIII, preferably cobalt, iron and chromium. In some POA cases, framework substitution is usable, but may not provide greatly improved activity.

The oxidation is usually carried out in the presence of a solvent. The solvent should have a polar aqueous component such as water or acetic acid plus an organic component to dissolve the alkane, e.g. mono or o-dichlorobenzene. If the proportions of these components are properly selected, a single phase homogeneous system results although this is not always critical. Thus in one procedure the HPA is dissolved in 0.1 ml $H_2O$ and 1-10 mls. of glacial acetic acid and the catalyst is then added resulting in a brightly colored solution. Then 10 mls of monochlorobenzene is added followed by the alkane. These proportions give a homogeneous system. Alternatively, the solvent can be acetic acid or water alone which will result in a heterogeneous oxidation. Acetonitrile has also been found to be an effective solvent in some cases.

The oxidation is carried out at 50°-250° C., in many cases 50°-200° C., more preferably 125°-175° C., and the low temperature is an advantage of the invention. The pressure is 0-5000 psig, adequate to maintain the liquid phase. Reaction time is 0.1-10 hours depending on conditions and is readily selected by the skilled worker. The amount of catalyst employed is generally 0.0001-1.0 mmoles catalyst per mole of reactant, preferably 0.001-0.1 but is always a catalytically effective amount.

The alkane starting materials include straight and branched-chain compounds having from about 1-20 carbon atoms, preferably 1-10 carbon atoms, such as methane, ethane, propane, n-butane, isobutane, n-pentane, n-hexane, 2-methylpentane, 3-methylpentane, heptane, 2-methylheptane, 3-methylheptane and the like, as well as cycloalkanes having from about 5-20 carbon atoms, preferably 5-10 carbon atoms, such as cyclopentane, cyclohexane, cycloheptane, cyclooctane, and the like. These compounds, if desired, may be substituted with various moieties, although care should be taken to exclude substituents which will adversely affect the activity of the catalyst.

As noted above, our process is highly selective for alcohols and extremely selective for alcohols and ketones, selectivity being defined as the mole percentage of the alkane reacted which is converted to the desired product. In our process the selectivity to alcohol is usually over 40%, often over 60%, and in some cases over 80%. The selectivity to alcohol and ketone is usually over 90%, frequently over 95%, a truly outstanding result. Insignificant traces of acetates are sometimes formed. The amount of carbon oxides formed is generally under 2%, usually less than 1% and is often under 0.2-0.5%, the percentages being expressed as the mole percent yield of carbon oxides based on the reacted alkane.

The following examples illustrate the invention more specifically. Initial examples show the preparation of typical HPAs and POAs, and subsequent examples show their use in alkane oxidation.

EXAMPLE 1

Preparation of 6-tungsto-6 vanadophosphoric acid, $H_9[PW_6V_6O_{40}] \cdot nH_2O$ 16.75 g (0.137 mole) of $NaVO_3$, 45.1 g (0.115 mole) of $Na_2WO_4 \cdot 2H_2O$ and 13.4 g (0.051 mole) $Na_2HPO_4 \cdot 7H_2O$ was added to 250 ml distilled water and the mixture was heated for 3 hrs. at 85° C. HCl was added to the cooled, filtered solution, and after partial evaporation, the orange-red crystalline product was obtained.

This is a general procedure for all of the various tungstovanadophosphoric acids, using the appropriate stoichiometric ratios of P/W/V to obtain the desired material.

The above product, and HPAs and POAs in general, can be identified by a combination of elemental analysis, which verifies the component ratios, and IR. The latter has a distinctive M—O stretching region from, for Keggin structures, $600-1200^{-1}$.

EXAMPLE 2

Preparation of 4-molybdo-8-vanadophosphoric acid, $H_{11}[PMo_4V_8O_{40}] \cdot nH_2O$ A mixture of 8.52 g (0.6 mole) of $Na_2HP_4$, 34.6 g (0.24 mole) of $MoO_3$, 59.0 g of $V_2O_5$ (0.32 mole) and 9.65 g of $Na_2CO_3$ was added to 400 ml of water and the resulting slurry is heated under reflux for 2 hrs. After filtering the solution, sulfuric acid was added and the solution evaporated, to produce the product.

This procedure is general for $H_x[PMo_yV_zO_{40}]$ by adjusting the stoichiometry of the added P, Mo, and V precursors.

EXAMPLE 3

Preparation of $K_5[PW_{11}V(4+)O_{40}]$ 45.0 g of 12-tungstophosphoric acid is dissolved in 105 ml of water. With stirring, the pH is adjusted to about 5.2 with potassium bicarbonate. The mixture is heated to 70° and 6.0 g of $VOSO_4$ in 15 ml of $H_2O$ is added. The solution is cooled and KCl is added to precipitate the product.

EXAMPLE 4

Preparation of $K_4[PW_{11}V(5+)O_{40}]$

The above preparation is followed except that 2.64 g of sodium metavanadate in 15 ml of $H_2O$ is added instead of $VOSO_4$.

EXAMPLE 5

Preparation of $K_6[PW_{11}Mn(2+)N_3O_{39}]$ 20.9 g of $K_5[PW_{11}Mn(+2)O_{39}]$ is dissolved in 150 ml of $H_2O$ while heating to 60°. Next, 20.0 g of $NaN_3$ in 50 ml of $H_2O$ is added, and the mixture is stirred with heating for 4 hrs. The material is evaporated to dryness and the product washed with methanol to remove any unreacted $NaN_3$. IR shows the N—N stretch of the bound azide at 2037 $cm^{-1}$.

Other HPAs and POAs can be treated in a similar way with $NaN_3$, $KN_3$ or $HN_3$ to produce azide complexes.

Examples 6-9 are the preparation of framework substituted polyoxoanions.

EXAMPLE 6

Preparation of $K_5[PW_{11}Fe(2+)O_{39}]$ 15.0 g of 12-tungstophosphoric acid is dissolved in 35 ml of $H_2O$. With stirring the pH is adjusted to about 5.2 with potassium bicarbonate. After heating to 70°, 1.45 g of ferrous sulfate in 10 ml of $H_2O$ is added. After cooling KCl is added to precipitate the product.

EXAMPLE 7

Preparation of $(NH_4)_5[PMo_{11}Co(2+)O_{39}]$ 20.0 g of 12-molybdophosphoric acid is dissolved in 50 ml of $H_2O$. This is heated to 70° while adjusting the pH to 4.5 with ammonium acetate. At this point 2.0 g of cobaltous acetate in 10 ml of water is added. The solution is cooled, filtered and precipitated as the ammonium salt by the addition of ammonium chloride.

EXAMPLE 8

Preparation of $(NH_4)_6[SiMo_{11}Co(2+)O_{39}]$ 20.9 g of 12. molybdosilicic acid is dissolved in 50 ml of $H_2O$. This is heated with stirring to 70° and the pH is adjusted to 4.4 with ammonium acetate. At this point 2.0 g of cobaltous acetate in 10 ml of $H_2O$ is added. After cooling ammonium chloride is added to precipitate the product.

EXAMPLE 9

Preparation of $K_6[PW_9Fe_3O_{37}]$ 8.5 g of $Na_8H[PW_9O_{34}]$ is dissolved in 200 ml of pH 6 buffer (sodium acetate and dilute acetic acid). With stirring, 1.69 g of $Fe_3(CH_3CO_2)_6(OH)_2Cl$ in 50 ml of $H_2O$ is added. The solution is heated to 50° for 15 min. After cooling KCl is added to precipitate the product.

The following examples show the use of our catalysts in liquid phase oxidation of propane and isobutane. The procedure varied slightly in the various runs but is typically as follows:

The catalyst is 0.1 ml of water which is then diluted with 5 ml acetic acid. The alkane (0.1-0.2 moles) is dissolved in 25 ml of chlorobenzene and the reaction mixture pressured to 100-2000 psig with air or oxygen. In isobutane oxidation, 0.025 mmole of catalyst per mole of isobutane was used; propane oxidation employed 0.007-0.07 mmole catalyst per mole of propane, the actual amount being shown after the catalyst formula. The reaction is carried out at 80°-200° C. for 1-10 hours after which the reaction mixture is analyzed. In the table below TON/hr is the moles of product produced per hour per mole of catalyst used and N/A means not available. The products of propane oxidation are isopropyl alcohol and acetone; from isobutane they are t-butyl alcohol, and acetone. Traces of isopropyl and t-butylacetate by-product are formed from propane and isobutane respectively.

Runs 2 and 3, compared to Run 1, show the effect of promoting the phosphomolybdate catalyst with vanadium.

Runs 5, 6, 7 and 8, compared with Run 4, show the effect of promoting the phosphotungstate catalyst with vanadium.

Runs 9 and 10 show the suitability of the potassium salt of the vanadium-promoted phosphotungstate catalyst.

Runs 11 and 12 demonstrate the effect of vanadium on the phosphotungstate catalyst when oxidizing isobutane, even at a quite low temperature.

Runs 13-16 demonstrate the effect of vanadium on the phosphomolybdate catalyst when oxidizing isobutane.

Runs 17-21 show the effect of azide promotion; in Runs 17-19 of vanadophosphotungstate catalyst and in Runs 20-21 of a chromium framework substituted POA. It is of interest to note that Runs 18, 19, 20 and 21 employed only one-quarter the amount of catalyst as Runs 17 and 19.

Runs 22 and 23 show the effect of framework substitution as do Runs 24-29 on a different catalyst. Runs 28-29 do not show substantial improvement from the manganese nor do they show a detriment, and, in any event, the results would be expected to be better with vanadium promotion of the catalyst.

TABLE I

| Run | Alkane | Catalyst & Amount | Temp. °C. | Time Hrs | TON/hr | Selectivity alcohol | ketone |
|---|---|---|---|---|---|---|---|
| 1 | $C_3$ | $H_3PMo_{12}O_4$-.030 | 150 | 3 | 34 | 49 | 49 |
| 2 | $C_3$ | $H_{11}PMo_4V_8O_{40}$-.050 | 150 | 4 | 65 | 44 | 53 |
| 3 | $C_3$ | $H_{11}PMo_4V_8O_{40}$-.050 | 150 | 2 | 88 | 48 | 49 |
| 4 | $C_3$ | $H_3PW_{12}O_{40}$-.030 | 150 | 3 | 47 | 53 | 45 |
| 5 | $C_3$ | $H_9PW_6V_6O_{40}$-.040 | 150 | 3 | 240 | 42 | 55 |
| 6 | $C_3$ | $H_9PW_6V_6O_{40}$-.040 | 175 | 3 | 199 | 35 | 62 |
| 7 | $C_3$ | $H_9PW_6V_6O_{40}$-.040 | 150 | 1 | 225 | 55 | 43 |
| 8 | $C_3$ | $H_9PW_6V_6O_{40}$-.040 | 125 | 1 | 0 | — | — |
| 9 | $C_3$ | $K_5PW_{11}V(4+)O_{40}$-.040 | 150 | 3 | 168 | 47 | 50 |
| 10 | $C_3$ | $K_4PW_{11}V(5+)O_{40}$-.040 | 150 | 3 | 153 | 46 | 46 |
| 11 | i-$C_4$ | $H_3PW_{12}O_{40}$-.025 | 100 | 6 | 0 | — | — |
| 12 | i-$C_4$ | $H_6PW_9V_3O_{40}$-.025 | 100 | 6 | 29 | 87 | 12 |
| 13 | i-$C_4$ | $H_3PMo_{12}O_{40}$-.025 | 100 | 6 | 0 | — | — |
| 14 | i-$C_4$ | $H_7PMo_8V_4O_{40}$-.025 | 100 | 6 | 44 | 89 | 11 |
| 15 | i-$C_4$ | $H_9PMo_6V_6O_{40}$-.025 | 100 | 6 | 73 | 84 | 14 |
| 16 | i-$C_4$ | $H_{11}PMo_4V_8O_{40}$-.025 | 100 | 6 | 87 | 84 | 15 |
| 17 | $C_3$ | $K_5PW_{11}VO_{40}$-.040 | 150 | 3 | 153 | 46 | 51 |

TABLE I-continued

| Run | Alkane | Catalyst & Amount | Temp. °C. | Time Hrs | TON/hr | Selectivity alcohol | ketone |
|---|---|---|---|---|---|---|---|
| 18 | $C_3$ | $K_5PW_{11}VO_{40}$-.010 | 150 | 3 | 19 | N/A | N/A |
| 19 | $C_3$ | $K_6PW_{11}VO_{40}N_3$-.010 | 150 | 3 | 695 | 45 | 54 |
| 20 | $C_3$ | $K_4PW_{11}CrO_{39}$-.010 | 150 | 3 | 14 | N/A | N/A |
| 21 | $C_3$ | $K_5PW_{11}CrO_{39}N_3$-.010 | 150 | 3 | 762 | 49 | 49 |
| 22 | i-$C_4$ | $K_3PMo_{12}O_{40}$-.025 | 100 | 6 | 0 | — | — |
| 23 | i-$C_4$ | $K_4PMo_{11}CrO_{39}$-.025 | 100 | 6 | 46 | 84 | 15 |
| 24 | i-$C_4$ | $K_4SiMo_{12}O_{40}$-.025 | 100 | 6 | 0 | — | — |
| 25 | i-$C_4$ | $K_6SiMo_{11}FeO_{39}$-.025 | 100 | 6 | 23 | 86 | 13 |
| 26 | i-$C_4$ | $K_6SiMo_{11}CoO_{39}$-.025 | 100 | 6 | 0 | — | — |
| 27 | i-$C_3$ | $K_6SiMo_{11}CoO_{39}$-.025 | 150 | 3 | 14 | N/A | N/A |
| 28 | i-$C_4$ | $K_6SiMo_{11}MnO_{39}$-.025 | 100 | 6 | 0 | — | — |
| 29 | i-$C_3$ | $K_6SiMo_{11}MnO_{939}$-.025 | 150 | 3 | 14 | — | — |

The invention claimed is:

1. Catalyst having the formula $H_{(e+x)}(X_kM_nO_y)^{-e}(N_3)_x$ where X is a group IIIA-VIA element, M is a transition metal, k is 1-5, n is 5-30, y is 18-62, and x is 1-4, and polyoxoanions thereof.

2. Catalyst according to claim 1 wherein X is phosphorus, n is 12, and y is 40.

3. Catalyst having the formula $K_6PW_{11}MnN_3O_{39}$.

4. Catalyst having the formula $K_6PW_{11}VO_{40}N_3$.

5. Catalyst having the formula $K_5PW_{11}CrO_{39}N_3$.

* * * * *